US011633108B2

(12) United States Patent
Langton

(10) Patent No.: US 11,633,108 B2
(45) Date of Patent: Apr. 25, 2023

(54) TRANS-ILLUMINATIVE INTRAORAL DIAGNOSTIC LIGHTING SYSTEM AND METHOD OF USING

(71) Applicant: Sean M. Langton, Somerville, MA (US)

(72) Inventor: Sean M. Langton, Somerville, MA (US)

(*) Notice: Subject to any disclaimer, the term of this patent is extended or adjusted under 35 U.S.C. 154(b) by 303 days.

(21) Appl. No.: 17/071,244

(22) Filed: Oct. 15, 2020

(65) Prior Publication Data

US 2022/0117492 A1 Apr. 21, 2022

(51) Int. Cl.
A61B 5/00 (2006.01)
A61B 1/24 (2006.01)
A61B 1/04 (2006.01)

(52) U.S. Cl.
CPC .............. A61B 5/0088 (2013.01); A61B 1/04 (2013.01); A61B 1/24 (2013.01); A61B 5/0084 (2013.01); A61B 5/682 (2013.01); A61B 2560/0214 (2013.01); A61B 2562/0238 (2013.01)

(58) Field of Classification Search
CPC .......... A61B 5/0088; A61B 5/682; A61B 1/24
See application file for complete search history.

(56) References Cited

U.S. PATENT DOCUMENTS

| 4,921,344 | A | 5/1990 | Duplantis |
| 8,989,567 | B1 | 3/2015 | Pulido et al. |
| 8,998,609 | B2 | 4/2015 | Prakash et al. |
| 9,301,672 | B2 | 4/2016 | Pulido et al. |
| 10,463,873 | B1* | 11/2019 | Yang ................... A61N 5/0603 |
| 10,542,946 | B2 | 1/2020 | Martin |
| 11,020,208 | B2* | 6/2021 | Pesach ................ A61B 5/0088 |
| 2001/0010538 | A1* | 8/2001 | Ooshima .............. A61B 1/0625 348/66 |
| 2008/0002402 | A1* | 1/2008 | Mandikos ............ A61C 19/003 433/29 |
| 2010/0020165 | A1* | 1/2010 | Crucs .................. H04N 5/23238 348/E7.085 |
| 2012/0003602 | A1 | 1/2012 | Waldmeier et al. |
| 2013/0330684 | A1* | 12/2013 | Dillon ................. A61C 19/003 433/29 |
| 2014/0132747 | A1* | 5/2014 | Andrews ............ A61B 1/00193 348/66 |
| 2014/0356802 | A1* | 12/2014 | Balog ..................... A61B 1/24 433/29 |
| 2017/0347943 | A1* | 12/2017 | Choi ..................... A61B 5/4552 |
| 2018/0125610 | A1* | 5/2018 | Carrier, Jr. ........... A61C 9/0053 |
| 2019/0183610 | A1* | 6/2019 | Raghavan ............... A61C 5/90 |
| 2019/0231492 | A1* | 8/2019 | Sabina ............. A61B 1/000094 |
| 2021/0220085 | A1* | 7/2021 | Khouri ................ A61B 1/0684 |

* cited by examiner

Primary Examiner — Nicholas D Lucchesi
(74) Attorney, Agent, or Firm — H. Jay Spiegel

(57) ABSTRACT

A trans-illuminative intraoral diagnostic lighting system includes a housing containing at least one LED and has a removable light diffusing positioning apparatus attached to it that facilitates proper positioning of the housing within the oral cavity of a person behind their teeth. When the LED(s) is/are activated, the oral cavity is illuminated and light passes through the teeth making their internal structures visible outside the oral cavity. A retractor may be used to retract the cheeks and lips to allow full exposure of the teeth and a camera may be employed to photograph the teeth from outside the oral cavity.

19 Claims, 6 Drawing Sheets

TRANS-ILLUMINATIVE INTRAORAL DIAGNOSTIC LIGHTING SYSTEM AND METHOD OF USING

BACKGROUND OF THE INVENTION

The present invention relates to a trans-illuminative intraoral diagnostic lighting system and method of using.

In the prior art, it is known to illuminate the interior of the oral cavity for various purposes associated with investigating diseases and other abnormalities of the oral cavity including the teeth.

Traditional methods to identify dental caries, intraoral pathology and to visualize the condition of internal tooth structures involve periodic irradiation of a patient's mouth to acquire diagnostic radiographs, otherwise known as X-rays. Radiographs that are acquired are employed by a dentist to identify existing intraoral pathology and to track the progression of incipient dental lesions as well as other intraoral pathology.

As is known, even the best X-rays provide low definition, black and white images of the internal structures of teeth and underlying hard tissues. Even in more modern systems that employ color images, the definition still remains quite low. Presently, there is no readily available solution to acquire radiation-free, high quality, full color diagnostic images of the internal structures of multiple teeth, across multiple arches, simultaneously as well as of the surrounding soft tissues. It is with this deficiency that the present invention was developed.

The natural translucency of teeth makes it possible for a sufficiently intense light to shine through the teeth and allow an image to be taken on the opposite side of the teeth from the location of the source of the light. This concept has never, to Applicant's knowledge, been taken advantage of in an effort to obtain images of teeth for diagnostic purposes. While transillumination has been used in dentistry for a long time, no-one, to the best of Applicant's knowledge has ever used, created or conceptualized a trans-illuminative diagnostic lighting system and method of use such as disclosed herein. This concept is central to the teachings of the present invention.

In the prior art, it is known to attempt to illuminate plural teeth for the purpose of taking images. However, such techniques focus on providing a source of light outside the mouth and photographing the image seen from outside the mouth of the teeth that are so-illuminated. Such an image is shown in FIG. 6. However, such an image is not able to see internal structures of the teeth even if the light employed is somewhat bright. The present invention addresses this deficiency in the prior art.

Additionally, in the prior art, it is known to insert a small intraoral camera within the oral cavity to take images therewithin. Some of these intraoral cameras utilize transillumination to detect insipient, interproximal lesions on 1-2 posterior teeth at a time on the same side of the teeth as that of the source of transillumination. Such images may detect various legions or other diseases of the oral cavity but are unable to detect abnormalities in high definition, across multiple teeth or across multiple arches. The present invention addresses this deficiency by illuminating the teeth from within a closed mouth and photographing them from outside the oral cavity.

The following prior art is known to Applicant:
U.S. Pat. No. 4,921,344 to Duplantis
U.S. Pat. No. 8,989,567 to Pulido et al.
U.S. Pat. No. 8,998,609 to Prakash et al.
U.S. Pat. No. 9,301,672 to Pulido et al.
U.S. Pat. No. 10,542,946 to Martin
U.S. Published Application No. US 2012/0003602 A1 to Waldmeier et al.

Each of the listed patents teaches some aspect of using a mouthpiece or otherwise photographing the interior of the oral cavity. However, none of these patents teaches the details of the present invention including illuminating a closed oral cavity from within and photographing the oral cavity from outside thereof for diagnostic purposes.

SUMMARY OF THE INVENTION

The present invention relates to a trans-illuminative intraoral diagnostic lighting system and method of using. The present invention includes the following interrelated objects, aspects and features:

(1) In a first aspect, an appliance is provided which consists of a sealed housing having one or more light emitting diodes (LEDs) exposed. The housing includes portable and rechargeable power such as, for example, a battery, and a wireless receiver.

(2) A removable, light diffusing positioning apparatus is removably attachable to the housing and includes tabs that may be bitten down upon by the teeth of the user to facilitate accurately positioning the housing within the oral cavity behind the patient's teeth.

(3) A dental retractor is employed in the inventive method to retract the soft tissue of the cheeks and lips so that a full view of the teeth and gums of the patient is visible from outside. Additionally, a camera is employed as part of the inventive method.

(4) A portable switching mechanism is provided which includes an on-off switch, preferably a portable and rechargeable power source, and a transmitter which transmits at a frequency receivable by the receiver within the inventive housing. When the on-off switch is closed, a signal is transmitted to the receiver which causes closure of a circuit to activate the LEDs and illuminate the oral cavity of the patient behind his or her teeth.

(5) With the dental retractor in place and the oral cavity illuminated, the camera may be employed to photograph the teeth as backlit by the LEDs. When this procedure is completed, the on-off switch on the portable power source may be pushed again so that a signal is transmitted from the transmitter to the receiver resulting in deactivation of the LEDs.

As such, it is a first object of the present invention to provide a full mouth trans-illuminative intraoral diagnostic lighting system and method of using.

It is a further object of the present invention to provide such a system and method in which a sealed housing may be accurately positioned within the oral cavity of a patient behind the teeth thereof and illuminated to cause light to pass through the translucent teeth.

It is a yet further object of the present invention to provide such a system and method in which a dental retractor is employed so that the exterior surfaces of the teeth are exposed to outside the oral cavity.

It is a still further object of the present invention to provide such a system and method in which a removable light diffusing positioning apparatus may be removably attached to the housing to allow accurate positioning of the housing within the oral cavity.

It is a yet further object of the present invention to provide such a system and method in which a camera with preferably multiple flash attachments can be employed to create a clear image of the exterior of the teeth, exposed by the dental retractor, so that internal tooth structures and abnormalities within the tooth structure of the teeth and gums may be viewed, photographed, and studied.

It is a yet further object of the present invention to provide such a system and method in which the entire set of both maxillary and mandibular teeth of a patient may simultaneously be photographed as illuminated from behind for the purposes of the present invention.

These and other objects, aspects and features of the present invention will be better understood from the following detailed description of the preferred embodiment when read in conjunction with the appended drawing figures.

SPECIFIC DESCRIPTION OF THE PREFERRED EMBODIMENT

Figure 1:
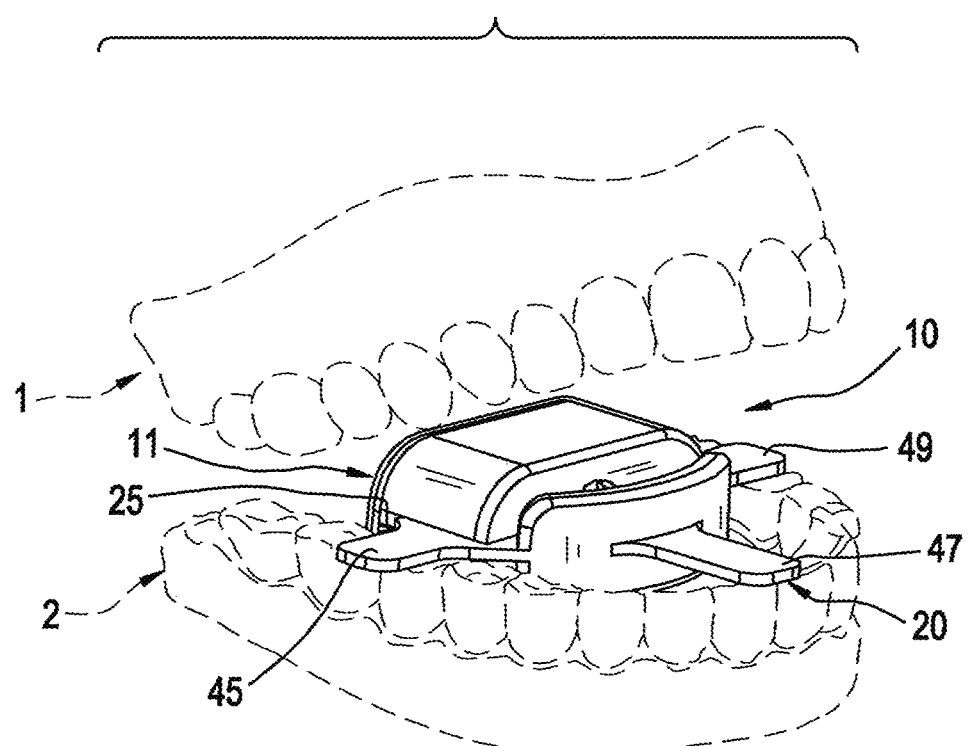
FIG. 1 shows a perspective view of the inventive housing and removable light diffusing positioning apparatus within the oral cavity of a patient.

With reference first to FIG. 1, the upper maxillary arch 1 and the lower mandibular arch 2 of a patient are shown with the inventive appliance 10 placed therein. The appliance 10 has a sealed housing 11 and a removable light diffusing positioning appliance 20 is shown connected thereto.

Figure 2:
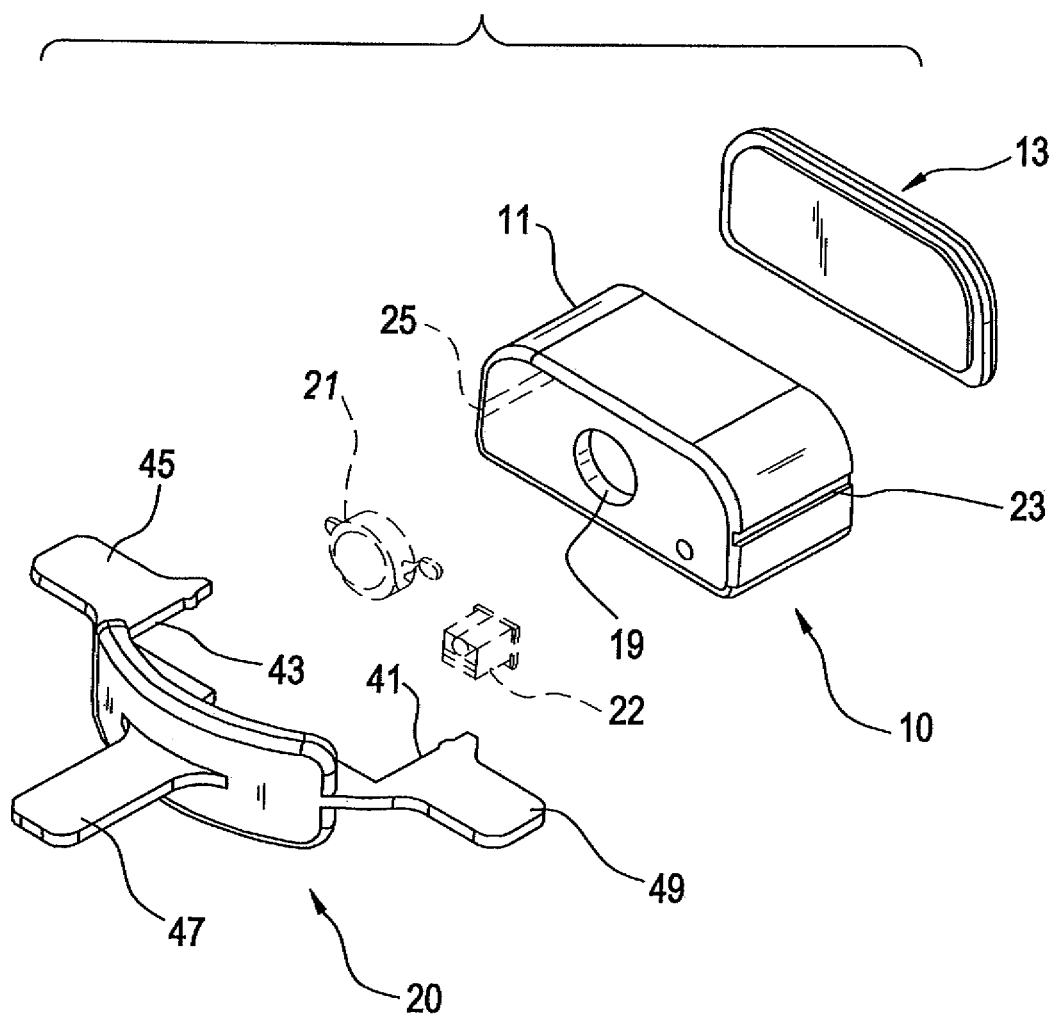
FIG. 2 shows an exploded perspective view of the housing and removable light diffusing positioning apparatus.
Figure 3:
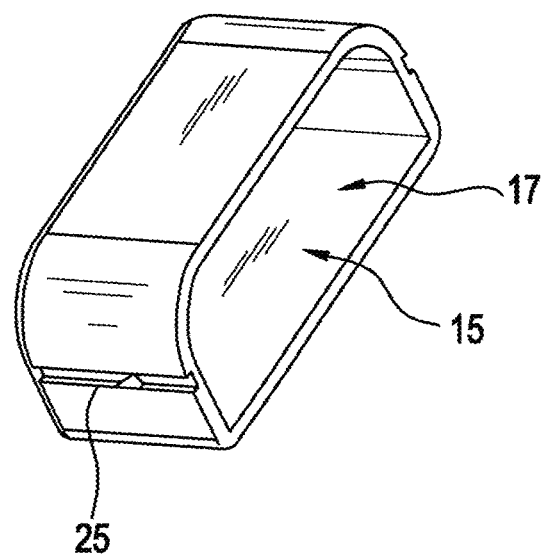
FIG. 3 shows a perspective view of the housing from a different angle than that of FIG. 2.

With reference to FIG. 2, the housing 11 includes a sealable wall 13 which closes an opening 15 (FIG. 3) to an internal chamber 17. The housing 11 includes an opening 19 which receives at least one light emitting diode (LED) 21 (FIG. 2), and a circuit board (not shown in FIG. 2) which is electrically connected to the LED 21. A USB port 22 permits recharging of a battery 27 within the housing 11. See FIG. 5 which shows the circuit including the battery 27.

Figure 5:
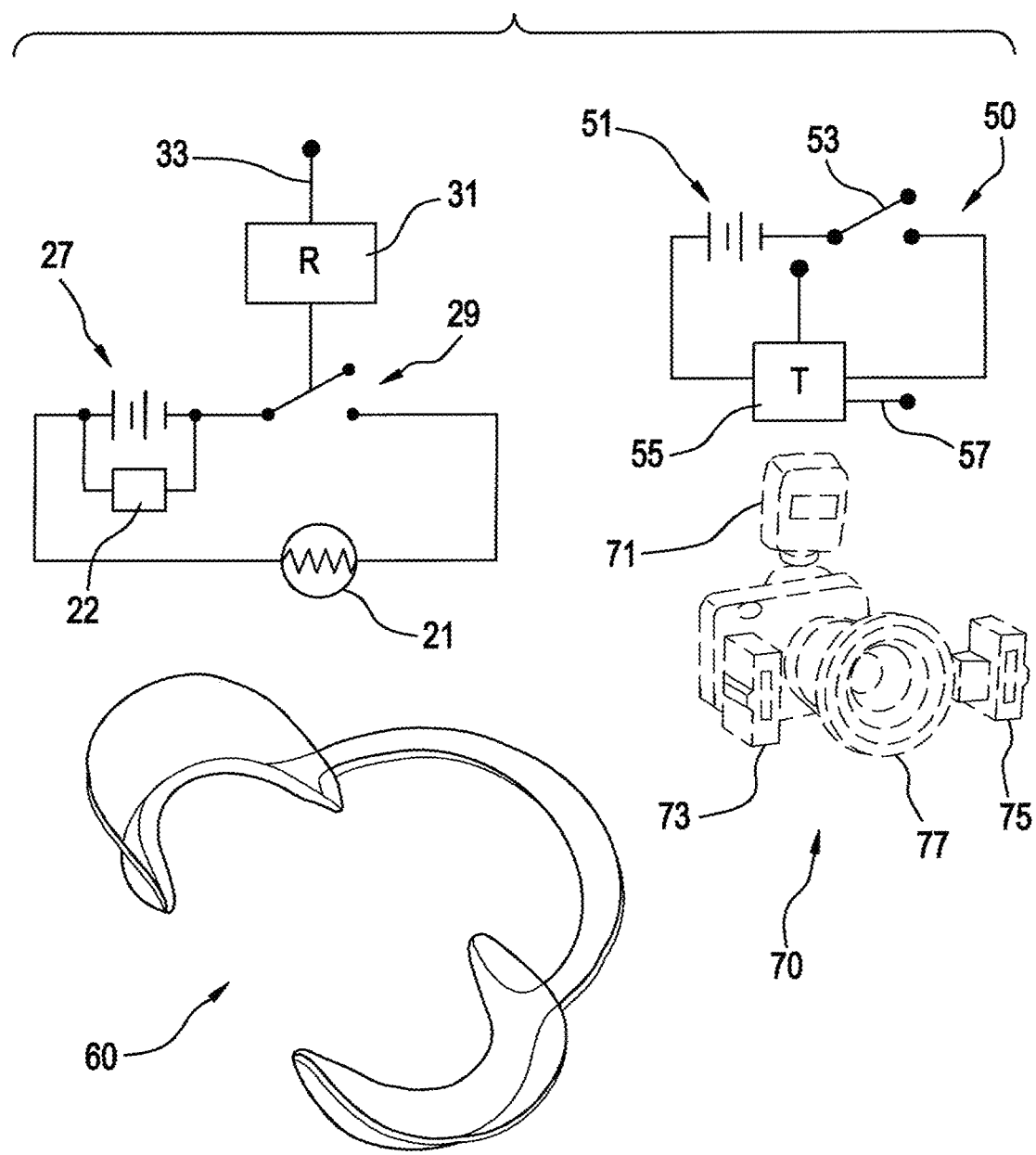
FIG. 5 shows a schematic representation of the components of the present invention utilized in practicing the inventive method.
Figure 6:
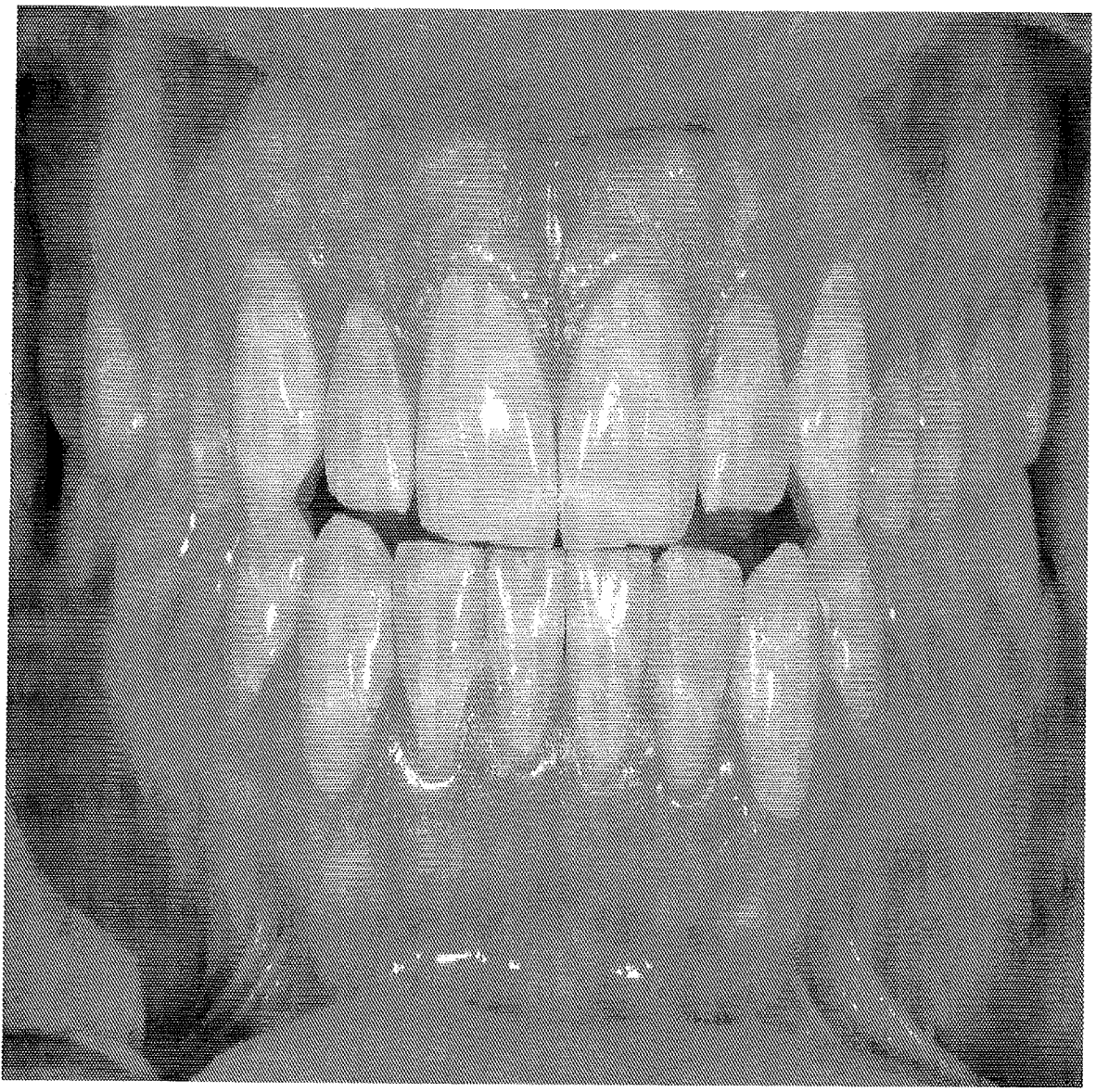
FIG. 6 shows a prior art image of the teeth of a patient taken from outside the oral cavity without internal illumination.

The housing 11 includes two side slots 23 and 25 for a purpose to be described in detail hereinafter. Contained within the housing, with reference to FIG. 5, are a rechargeable battery 27, a switch 29, and a wireless receiver 31 with an antenna 33. The housing 11 may be disinfected for re-use.

The slots 23 and 25 are provided to facilitate assembly of the removable light diffusing positioning apparatus 20. The removable light diffusing positioning apparatus 20 has facing surfaces 41 and 43 (FIG. 2) which are respectively received within the slots 23 and 25 to assemble the removable light diffusing positioning apparatus 20 to the housing 11 in the manner shown in FIG. 1.

The removable light diffusing positioning apparatus 20 includes three tabs 45, 47 and 49 which are sized to sit between the teeth of the patient as shown in FIG. 1 to facilitate positioning the housing 11 in the desired location within the oral cavity and to stabilize the position of the patient's biting position. With the device 10 and the positioner 20 positioned as shown in FIG. 1, the jaw may be closed so that the teeth of the maxillary arch engage the upper surfaces of the tabs 45, 47 and 49 to secure the device 10 in the position shown in FIG. 1 within the oral cavity.

When this occurs, the LED 21 or plural LEDs, as the case may be, may be illuminated in the manner explained below.

Figure 4:
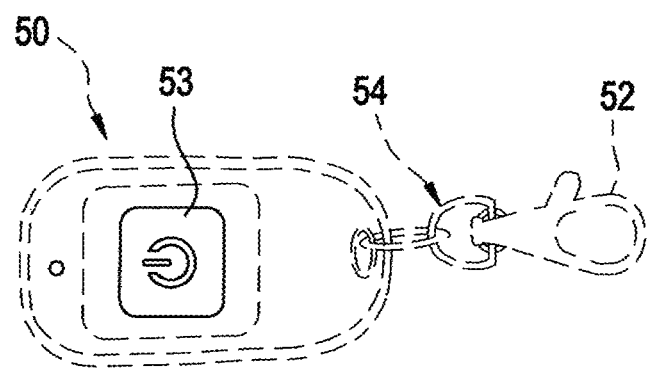
FIG. 4 shows a top view of the actuator for the LEDs.

With reference back to FIG. 5, the activator for the LED 21 consists of a device 50 which consists of a battery 51, a switch 53, a transmitter 55, and an antenna 57, all within a single circuit. The device 50 is also seen in FIG. 4 with its actuator button 53 shown. If desired, a clip 52 may be attached via a tether 54 as shown in FIG. 4.

The transmitter 55 has a frequency of transmission which may be received by the receiver 31. Thus, when the switch 53 is closed, the battery 51 supplies power to the transmitter 55 which then transmits a signal via the antenna 57, which signal is received by the antenna 33 of the receiver 31. When that signal is received, the switch 29 is closed to activate the LED 21 or plural LEDs with power supplied by the battery 27.

As should be understood by those skilled in the art, when it is desired to deactivate the LED 21 or LEDs, the switch 53 is opened. When it is opened, the signal from the transmitter 55 ceases to operate and thus the receiver 31 no longer receives that signal, thereby causing the switch 29 which is biased to the open position to open, thereby turning off the LED 21 or LEDs.

Also shown in FIG. 5 is a dental retractor 60 and a camera 70 which includes exemplary flash attachments 71, 73 and 75 along with a lens 77.

In practicing the method of the present invention, the dental retractor 60 is utilized in the manner understood by those skilled in the art to retract the cheeks and lips away from the teeth so that the teeth and gums are clearly visible outside the oral cavity. The housing 11 is placed in the oral cavity in the orientation shown in FIG. 1 with the removable light diffusing positioning apparatus 20 placed in the manner shown. The upper maxillary teeth 1 and lower mandibular teeth 2 converge by having the patient close his or her jaw onto tabs 45, 47 and 49 to securely position the housing 11 in the orientation shown in FIG. 1.

Figure 7:
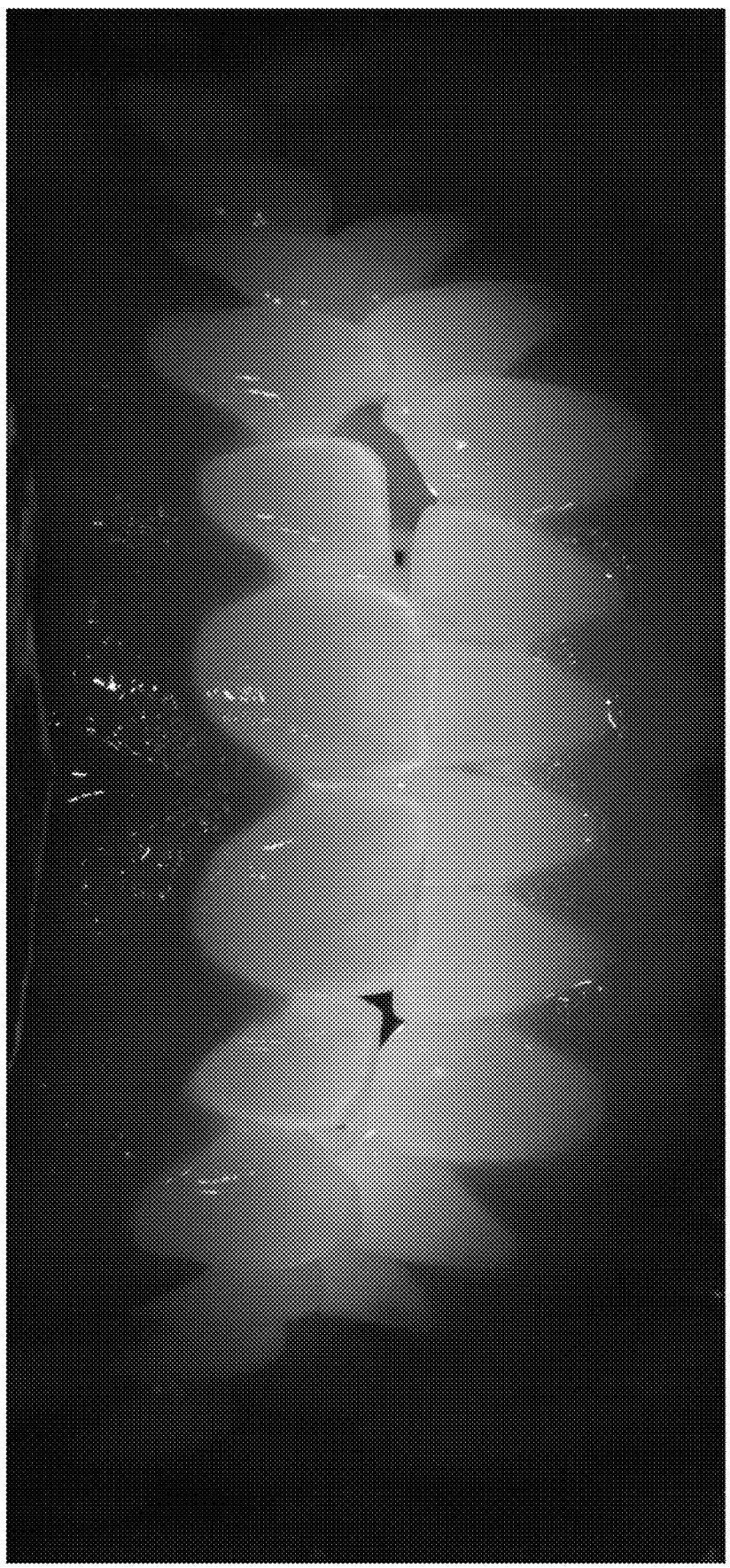
FIG. 7 shows an image of the same teeth taken in accordance with the teachings of the present invention.

Thereafter, the switch 53 is closed and a signal transmitted from the transmitter 55 to the receiver 31 closing the switch 29 and activating the LED 21 or LEDs to strongly illuminate the interior of the oral cavity including shining light through the translucent teeth as shown in FIG. 7. Thereafter, the camera 70 is employed to take photographs which correspond to the image shown in FIG. 7 capturing images of the translucent teeth so that interior structures and abnormalities can be clearly visible.

The present invention is advantageous over the prior art because it is radiation free. It utilizes trans-illumination to help detect existing intraoral pathology of both the hard and soft tissues and enables tracking of the progression intraoral pathology. Additionally, the present invention enables providing of trans-illuminated images of the hard and soft tissues of the entire mouth which are recognizable to the patient and which can be utilized for improved communication between the dentist and the patient. Additionally, the present invention allows for improved communication between a dentist and lab technicians in the accurate fabrication of ceramic restorations such as crowns, veneers and bridges. In the preferred embodiment, the removable light diffusing positioning apparatus 20 is translucent so that it can evenly diffuse any harsh light immediately emitted from the LED. This even diffusion of light through the removable light diffusing positioning apparatus allows the clearest images to be captured of both hard and soft tissues in the oral cavity.

Through utilization of the present invention, a dentist can easily and inexpensively maintain records of the progression of diseases of the teeth and gums and properly communicate and advise a patient regarding any necessary or recommended treatments. In addition, through utilization of the present invention, a dentist can easily and inexpensively communicate highly detailed instructions to any dental technician involved in the fabrication of ceramic restorations such as crowns, veneers or bridges.

In the preferred embodiment of the present invention, the LED 21 or LEDs emit light within the visible spectrum at a wavelength of approximately 380 nm-740 nm and within the near infrared spectrum at a wavelength of approximately 740 nm-2500 nm, which is the wavelength range that has been found by Applicant to best facilitate creation of images of the teeth illuminated from within the oral cavity. The housing 11 is sealed and can be disinfected so that it can be re-used. The housing 11 in the preferred embodiment has a length of about 6.5 centimeters, a width of about 2.5 centimeters, and a depth of between 1 and 3 millimeters as necessary so that it can contain the required electrical components. Preferably, the entire device should be as small as possible.

The removable light diffusing positioning apparatus 20 as well as the housing 11 also act as a tongue stop to keep the tongue out of the way when images are being taken. The tabs 45, 47 and 49 are designed to extend sufficiently far enough away from the housing 11 so that they can overlie the teeth of the patient's lower dentition and can be bitten on when the upper maxillary and lower mandibular dentitions 1 and 2 converge together. Biting on the tabs 45, 47 and 49 during the process stabilizes the removable light diffusing positioning apparatus 20 and the housing 11 inside the patient's mouth.

In the preferred embodiment, the LED 21 may, in fact, be a plurality of LEDs or LED strips mounted about the face of the housing 11 and spaced apart a desired distance based upon the manner by which the user wishes to illuminate the interior of the oral cavity. These positions may be adjustable as desired.

The camera 70 shown in FIG. 5 may be any desired camera which preferably creates digital images that may be electronically transmitted and viewed. In the preferred embodiment, multiple flash devices 71, 73 and 75 are employed but any flash devices which can facilitate creation of clear images of the teeth may suitably be employed. Any dental retractors such as the dental retractor 60 may suitably be employed.

As such, an invention has been disclosed in terms of a preferred embodiment thereof which fulfills each and every one of the objects of the invention as set forth hereinabove, and provides a new and useful trans-illuminative intraoral diagnostic lighting system and method of using of great novelty and utility Of course, various changes, modifications and alterations in the teachings of the present invention may be contemplated by those skilled in the art without departing from the intended spirit and scope thereof.

As such, it is intended that the present invention only be limited by the terms of the appended claims.

The invention claimed is:

1. A trans-illuminative intraoral diagnostic lighting system, comprising:

a) a sealed housing sized to fit within a person's oral cavity behind the person's teeth;
b) a source of light carried by the housing and, when activated, shining light within said oral cavity;
c) a separate positioning apparatus removably connected to said housing and configured to orient said housing in a desired position within said oral cavity, said positioning apparatus comprising a plurality of tabs extending outwardly from said housing and configured to be clenched between upper and lower teeth of said person to hold said upper and lower teeth in close proximity and position said housing in a desired position and assist said person in stabilizing their bite for photo taking;
d) a first source of power connected to said source of light; and
e) a first on-off switch which when closed activates said source of light and causes light to illuminate said oral cavity and illuminate said teeth so that images of said teeth as backlit by said source of light may be taken from outside said oral cavity.

2. The trans-illuminative intraoral diagnostic lighting system of claim 1, wherein said first source of power comprises a rechargeable battery contained within said housing.

3. The trans-illuminative intraoral diagnostic lighting system of claim 2, wherein said first on-off switch is located outside said oral cavity.

4. The trans-illuminative intraoral diagnostic lighting system of claim 3, wherein said first on-off switch is connected to a wireless transmitter and further including a wireless receiver is contained within said housing and connected to a second on-off switch, whereby closure of said first on-off switch causes said transmitter to transmit a signal to said receiver, causing closure of said second on-off switch and activation of said source of light.

5. The trans-illuminative intraoral diagnostic lighting system of claim 4, wherein said source of light comprises a light emitting diode (LED).

6. The trans-illuminative intraoral diagnostic lighting system of claim 5, wherein said LED comprises a plurality of LEDs.

7. The trans-illuminative intraoral diagnostic lighting system of claim 4, wherein said first on-off switch and transmitter are contained within a further housing, said transmitter and first on-off switch connected to a second source of power.

8. The trans-illuminative intraoral diagnostic lighting system of claim 7, wherein said second source of power comprises a further battery contained within said further housing.

9. The trans-illuminative intraoral diagnostic lighting system of claim 2, wherein said housing has a sealable wall which when removed permits access to an internal chamber within said housing containing said battery.

10. The trans-illuminative intraoral diagnostic lighting system of claim 1, wherein said positioning apparatus diffuses light and is fabricated of a translucent material.

11. The trans-illuminative intraoral diagnostic lighting system of claim 1, further including, in combination, a dental retractor for retracting cheeks and lips of said person to expose forward facing surfaces of said teeth and of gums of said person from outside said oral cavity.

12. The trans-illuminative intraoral diagnostic lighting system of claim 11, further including, in combination, a camera for photographing said teeth as illuminated by said source of light.

13. The trans-illuminative intraoral diagnostic lighting system of claim 12, wherein said camera includes a flash device which activates during taking of a photograph.

14. The trans-illuminative intraoral diagnostic lighting system of claim 12, wherein said source of light comprises a light emitting diode (LED).

15. The trans-illuminative intraoral diagnostic lighting system of claim 14, wherein said LED comprises a plurality of LEDs.

16. A method of obtaining photographic images of teeth of a person, including the steps of:
  a) providing a trans-illuminative intraoral diagnostic lighting system including:
    i) a sealed housing sized to fit within said person's oral cavity behind the person's teeth;
    ii) a source of light carried by the housing and, when activated, shining light within said oral cavity;
    iii) a separate positioning apparatus removably connected to said housing and configured to orient said housing in a desired position within said oral cavity, said positioning apparatus comprising a plurality of tabs extending outwardly from said housing and configured to be clenched between upper and lower teeth of said person to hold said upper and lower teeth in close proximity and position said housing in a desired position and assist said person in stabilizing their bite for photo taking;
    iv) a source of power connected to said source of light; and
    v) an on-off switch which when closed activates said source of light and causes light to illuminate said oral cavity and illuminate said teeth so that images of said teeth as backlit by said source of light may be taken from outside said oral cavity;
  b) providing a dental retractor;
  c) providing a camera;
  d) placing said sealed housing within said oral cavity of said person, behind said teeth;
  e) retracting cheeks and lips of said person using said dental retractor;
  f) activating said source of light; and
  g) using said camera to photograph outer surfaces of said teeth.

17. The method of claim 16, wherein said source of light comprises at least one light emitting diode (LED).

18. The method of claim 17, wherein said camera includes a flash device.

19. The method of claim 16, wherein said source of power is contained within said sealed housing.

* * * * *